United States Patent

Howell

Patent Number: 4,608,435
Date of Patent: * Aug. 26, 1986

[54] BENZO-1,4-QUINONES

[75] Inventor: Frederick H. Howell, Atherton, England

[73] Assignee: Ciba-Geigy AG, Basel, Switzerland

[*] Notice: The portion of the term of this patent subsequent to Nov. 20, 2001 has been disclaimed.

[21] Appl. No.: 489,360

[22] Filed: Apr. 28, 1983

[30] Foreign Application Priority Data

May 5, 1982 [GB] United Kingdom ............... 8212970

[51] Int. Cl.$^4$ .................. C07C 50/00; C07D 265/32; C07D 413/00

[52] U.S. Cl. .................................. 544/87; 544/111; 544/173; 546/189; 546/226; 548/524; 548/571; 549/414; 549/415; 549/420; 549/426; 549/427; 549/472; 549/473; 549/475; 549/480; 549/493; 549/501; 260/396 R; 260/396 N

[58] Field of Search ................. 260/396 R, 396 N; 544/111, 87, 173; 549/472, 415, 414, 420, 426, 427, 473, 475, 480, 493, 501; 546/189, 226; 548/524, 571

[56] References Cited

U.S. PATENT DOCUMENTS

| | | | |
|---|---|---|---|
| 2,927,932 | 3/1960 | Preston | 260/396 R |
| 3,957,836 | 5/1976 | Morimoto et al. | 260/396 R |
| 4,086,253 | 4/1978 | Hopper et al. | 260/396 N |
| 4,484,000 | 11/1984 | Howell | 549/415 |

FOREIGN PATENT DOCUMENTS

| | | |
|---|---|---|
| 0021841 | 1/1981 | European Pat. Off. |
| 2103615 | 2/1983 | United Kingdom |

OTHER PUBLICATIONS

Morrison & Boyd, *Organic Chemistry*, 1974, p. 878.

Abrahart, *Dyes and Their Intermediates*, 1968, 7–9.

*Primary Examiner*—Glennon H. Hollrah
*Assistant Examiner*—Raymond Covington
*Attorney, Agent, or Firm*—Wenderoth, Lind & Ponack

[57] ABSTRACT

New benzo-1,4-quinones and salts thereof with organic or inorganic acid and bases have the formula I

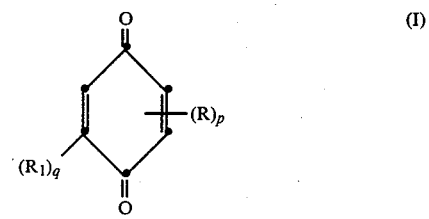

wherein p is 1 or 2 and q is 0 or 1, provided that p+q is 1 or 2, R is a residue of formula II

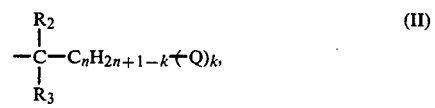

wherein Q is selected from the residues $-CO_2R_4$, $-CON(R_4)(R_5)$, $-OR_5$, $-OCOR_7$, $-N(R_8)(R_9)$, $-PO(OR_{10})([O]_xR_{11})$, $-SO_2R_{12}$, $-CN$, Halogen, $-NO_2$ or $-COR_{13}$, n is an integer from 1 to 20, k is 1 or 2 and x is 0 or 1, and $R_1$ to $R_5$ and $R_7$ to $R_{13}$ are as defined in the specification.

The compounds of formula I are useful in photographic materials such as bleaching inhibitors in films of photographic silver dye bleach materials.

8 Claims, No Drawings

BENZO-1,4-QUINONES

The present invention relates to new benzo-1,4-quinones and to a process for their preparation.

According to the present invention, there are provided novel benzo-1,4-quinones of the formula I

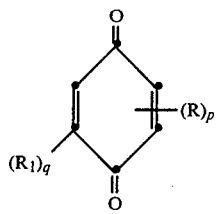

where p is 1 or 2 and q is 0 or 1, provided that p+q is 1 or 2;

R is a residue of formula II

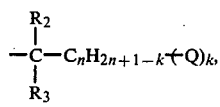

and

Q is selected from the residues $-CO_2R_4$, $-CON(R_4)(R_5)$, $-OR_5$, $-OCOR_7$, $-N(R_8)(R_9)$, $-PO(OR_{10})([O]_xR_{11})$, $-SO_2R_{12}$, $-CN$, Halogen, $-NO_2$ or $-COR_{13}$, n is an integer from 1 to 20, k is 1 or 2 and x is 0 or 1, $R_1$ is $C_1$-$C_8$ straight- or branched chain alkyl, or a residue of formula II as hereinbefore defined, and when $R_1$ is a residue of formula II, then $R_1$ and R may be the same of different;

$R_2$ and $R_3$ are the same or different and each is straight or branched chain alkyl group having from 1 to 5 carbon atoms and, when Q is $-CO_2R_4$, either $R_2$ or $R_3$ is optionally substituted by a $-CO_2R_4$ group, the $R_4$ groups being independent, or $R_2$ or $R_3$ may be so linked to the residue $C_nH_{2n+1-k}$ that there is formed a $C_5$-$C_{12}$ cycloalkylene residue substituted by the group $-(CO_2R_4)_k$, the $R_4$ groups being independent, $R_4$ independently is H, a straight or branched chain alkyl having from 1 to 20 carbon atoms, optionally interrupted by 1 to five oxygen atoms and optionally substituted by a group $-OR_6$ wherein $R_6$ is $C_3$-$C_{12}$ cycloalkyl, straight or branch $C_3$-$C_{20}$ alkenyl, $C_6$-$C_{10}$ aryl optionally substituted by one or two $C_1$-$C_4$ alkyl groups or $C_7$-$C_{13}$ aralkyl, or $R_4$ is a divalent straight- or branched chain alkylene group having 2 to 20 carbon atoms, a straight or branched chain alkenyl group having from 3 to 20 carbon atoms, a cycloalkyl group having from 3 to 12 carbon atoms; an aryl group having from 6 to 10 carbon atoms optionally substituted by a $C_1$-$C_4$ alkyl group; or an aralkyl group having from 7 to 13 carbon atoms; a 5 or 6 membered heterocycle containing an oxygen atom, and optionally substituted by one or two $C_1$-$C_4$ straight- or branched chain alkyl groups; or methyl substituted by a 5 or 6 membered heterocycle containing an oxygen atom and optionally substituted by one or two $C_1$-$C_4$ straight- or branched chain alkyl groups;

$R_5$ is hydrogen or a straight or branched chain alkyl group having from 1 to 20 carbon atoms, or $R_4$ and $R_5$ together with the nitrogen atom to which they are each bonded may form a 5 or 6 membered heterocyclic ring, optionally substituted by one or two $C_1$-$C_4$ alkyl groups, $R_7$ is H or a straight- or branched chain alkyl group having from 1 to 20 carbon atoms, a straight- or branch chain alkenyl having from 3 to 20 carbon atoms, a $C_3$-$C_{12}$ cycloalkyl group, a $C_7$-$C_{13}$ aralkyl group, or a $C_6$-$C_{10}$ aryl group, optionally substituted by one or two $C_1$-$C_4$ alkyl groups;

$R_8$ is H or a straight- or branched chain alkyl group having from 1 to 4 carbon atoms and $R_9$ is H, a straight- or branched chain alkyl group having 1 to 4 carbon atoms, or an acyl group of formula $-COR_7$ wherein $R_7$ has its previous significance, or $R_8$ and $R_9$, together with the nitrogen atom to which they are each bonded, form a 5- or 6-membered ring, optionally substituted by one or two $C_1$-$C_4$ alkyl groups; and when x is 1 $R_{10}$ and $R_{11}$ are the same or different and each is H or a straight or branched chain alkyl group having from 1 to 20 carbon atoms: or $R_{10}$ and $R_{11}$ may be linked together to form a $C_2$-$C_3$ alkylene chain optionally substituted by one to four $C_1$-$C_{20}$ alkyl groups; and when x is 0, $R_{10}$ is H or a straight or branched chain alkyl group having from 1 to 20 carbon atoms and $R_{11}$ is a $C_1$-$C_5$ straight chain alkyl group;

$R_{12}$ is $-OH$, Cl, $-N(R_5)(R_7)$ wherein $R_5$ and $R_7$ have their previous significance; $R_{13}$ is $-H$, a straight- or branched chain alkyl group having 1 to 20 carbon atoms or halogen, provided that, when $R_{12}$ is $-OH$, then $R_1$ is a residue of formula II, and salts thereof with organic or inorganic acids and bases.

When the group $R_1$ is a $C_1$-$C_8$ straight- or branched chain alkyl group it may be, for example, a methyl, ethyl, n-propyl, isopropyl, n-butyl, iso-butyl, t-butyl, t-pentyl, or 1,1,3,3-tetramethylbutyl.

When the group $R_2$ or $R_3$ is a $C_1$-$C_5$ straight or branched chain alkyl group it may be, for example, a methyl, ethyl, n-propyl, isopropyl, n-butyl or sec.-butyl. $C_5$ alkyl groups $R_2$ or $R_3$ are n-pentyl or neopentyl groups, When the group $R_4$ is a $C_1$-$C_{20}$ straight or branched chain alkyl group optionally interrupted by one to 5 oxygen atoms it may be, for example, a methyl, ethyl, 2-methoxyethyl, 2-ethoxyethyl, 2-n-propoxyethyl, 2-n-butoxyethyl, n-pentyl, n-hexyl, n-heptyl, n-octyl, 2-ethylhexyl, n-nonyl, n-decyl, n-dodecyl, n-tetradecyl, n-hexadecyl, n-octadecyl, n-eicosyl, $-(C_2H_4O)_2CH_3$, $-(C_2H_4O)_3CH_3$, $-(C_2H_4O)_4CH_3$ or $-(C_2H_4O)_5CH_3$ group.

$C_2$-$C_{20}$ alkylene groups $R_4$ are e.g. $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_{10}-$, $-(CH_2)_{12}-$, $-(CH_2)_{14}-$, $-(CH_2)_{16}-$, $-(CH_2)_{18}-$ and $-(CH_2)_{20}-$, When $R_4$, $R_6$ or $R_7$ is a $C_3$-$C_{20}$ straight or branched chain alkenyl group, it may be for example, a prop-2-enyl, n-but-2-enyl, 2-methyl-prop-2-enyl, n-pent-2-enyl, n-hex-2-enyl, n-hexa-2,4-dienyl, n-dec-10-enyl, or n-eicos-2-enyl group.

When the group $R_4$, $R_6$ or $R_7$ is a $C_3$-$C_{12}$ cycloalkyl group, it may be, for example, a cyclopropyl, cyclobutyl, cyclopentyl, cyclohexyl, cyclooctyl, cyclodecyl, adamantyl, or cyclododecyl group. When the group $R_4$, $R_6$ or $R_7$ is a $C_7$-$C_{13}$ aralkyl group it may be, for example, a benzyl, phenylethyl, benzhydryl, or naphthylmethyl group.

When the group $R_4$, $R_6$ or $R_7$ is a $C_6$–$C_{10}$ aryl group optionally substituted by one or two $C_1$–$C_4$ straight or branched chain alkyl groups, it may be, a phenyl, tolyl, xylyl, cumyl, butylphenyl or naphthyl group.

When the group $R_4$ is a 5- or 6-membered heterocycle containing oxygen, and optionally substituted by one or two straight- or branch chain $C_1$–$C_4$ alkyl groups, it may be, for example, tetrahydrofuran-3-yl, tetrahydropyran-4-yl or 2,6-dimethyl-tetrahydropyran-4-yl. When the group $R_4$ is methyl substituted by a 5- or 6-membered heterocycle containing an oxygen atom, and optionally substituted by one or two straight- or branch chain $C_1$–$C_4$ alkyl groups, it may be, for example, furfuryl, tetrahydrofurfuryl or tetrahydropyran-2-yl-methyl.

When the group $R_8$ and $R_9$ is a $C_1$–$C_4$ straight or branched chain alkyl group it may be for example, a methyl, ethyl, n-propyl, isopropyl, n-butyl, or sec.-butyl group.

When the groups $R_4$ and $R_5$, and the groups $R_8$ and $R_9$, together with the nitrogen atom to which they are bonded form a 5- or 6-membered heterocyclic ring, optionally substituted by one or two $C_1$–$C_4$ alkyl groups, this ring may be a pyrrolidine, piperidine, morpholine or a 2,5-dimethyl morpholine ring.

When the groups $R_5$, $R_7$, $R_{10}$, $R_{11}$ or $R_{13}$ are $C_1$–$C_{20}$ straight or branched chain alkyl they may be the same or different and may be methyl, ethyl, n-propyl, iso-propyl, n-butyl, sec.-butyl, n-pentyl, n-hexyl, n-heptyl, n-octyl, 2-ethylhexyl, n-nonyl, n-decyl, n-dodecyl, n-tetradecyl, n-hexadecyl, n-octadecyl, or n-eicosyl groups.

When the groups $R_{10}$ and $R_{11}$ are linked to form a $C_2$ or $C_3$ methylene chain optionally substituted by one to four $C_1$–$C_{20}$ alkyl chains, they may be for example —CH$_2$CH$_2$—, —CH$_2$—CH$_2$—CH$_2$—, —CH$_2$CH(CH$_3$)—, —CH$_2$CH(C$_2$H$_5$)—, —CH$_2$CH(C$_{20}$H$_{41}$)—, —CH(CH$_3$)CH(CH$_3$)—, —CH—(CH$_3$)C(CH$_3$)$_2$—, —C(CH$_3$)$_2$C(CH$_3$)$_2$—, —CH$_2$CH$_2$—C(CH$_3$)$_2$—, or —CH(CH$_3$)CH$_2$CH(CH$_3$)— groups.

Examples of salts where Q is an acidic groups, e.g.—COOH, include salts with alkali and alkaline earth metals and amines and, where Q is a —N(R$_8$)(R$_9$) group, salts with organic and inorganic acids for example, hydrochloric, sulphuric, para-toluene-sulphonic and oxalic acids.

In one preferred embodiment, the groups R and $R_1$ are bonded in the 2- and 5- positions, respectively, in the benzo-1,4-quinones of formula I.

Other preferred compounds of the invention are those having the formula I, wherein $R_1$ is a group of formula III

wherein A is an alkyl group having from 1 to 5 carbon atoms. In the group R Q is preferably —CO$_2$R$_4$, —O-COR$_7$ or —CN, wherein $R_4$ and $R_7$ have their previous significance.

Particularly preferred are compounds of formula I, wherein Q is —CO$_2$R$_4$ and $R_4$ is an alkyl group having from 1 to 12 carbon atoms which is unsubstituted or substituted by a cycloalkyloxy group having from 3 to 12 carbon atoms or by an aryloxy group having from 6 to 10 carbon atoms, or $R_4$ is a cycloalkyl group having from 3 to 12 carbon atoms, aryl having from 6 to 10 carbon atoms, $C_7$–$C_{13}$ aralkyl or a methyl group substituted by a 5- or 6-membered heterocyclic ring containing an oxygen atom, or Q is —OCOR$_7$, wherein $R_7$ is —H, $C_1$–$C_{20}$ alkyl, $C_3$–$C_{12}$ cycloalkyl, $C_7$–$C_{13}$ aralkyl or unsubstituted $C_6$–$C_{10}$ aryl, $R_1$ is a group of formula II, wherein Q has its previous significance, $R_2$ and $R_3$, independently, are —H or $C_1$–$C_5$ alkyl, p and q are 1 and k and n have their previous significance.

Further particularly preferred compounds of formula I correspond to the formula IV

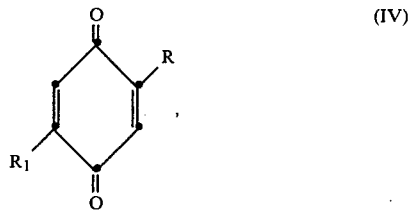

wherein R and $R_1$ are a group of formula II, wherein Q is —CO$_2$R$_4$ and $R_4$ is $C_1$–$C_8$ alkyl or $C_5$–$C_8$ cycloalkyl, or Q is —OCOR$_7$, wherein $R_7$ is —H or $C_1$–$C_4$ alkyl, $R_2$ and $R_3$ are each methyl, k is 1 and n is an integer from 1 to 10.

Still further preferred compounds of formula IV are those wherein R and $R_1$ are a group of formula II, Q is —CO$_2$R$_4$, $R_2$ and $R_3$ each are methyl, $R_4$ is $C_1$–$C_8$ Alkyl, k is 1 and n is 3.

Non-limiting examples of compounds of formula I include:

2-(3'-methoxycarbonyl-2'-methyl-prop-2'-yl)-1,4-benzoquinone 2-(3'-n-hexyloxycarbonyl-2'-methyl-prop-2'-yl)-1,4-benzoquinone 5-t-butyl-2-(3'-n-hexyloxycarbonyl-2'-methyl-prop-2'-yl)-1,4-benzoquinone 5-t-butyl-2-(3'-n-dodecyloxycarbonyl-2'-methyl-prop-2'-yl)-1,4-benzoquinone 2,5-bis-(3'-methoxycarbonyl-2'-methyl-prop-2'-yl)-1,4-benzoquinone 2,5-bis-(3'-n-hexyloxycarbonyl-2'-methyl-prop-2'-yl)-1,4-benzoquinone 2,5-bis-(3'-dodecyloxycarbonyl-2'-methyl-prop-2'-yl)-1,4-benzoquinone 2-(4'-methoxycarbonyl-1'-methyl-cyclohex-1'-yl)-1,4-benzoquinone 2-(4'-n-hexyloxycarbonyl-1'-methyl-cyclohex-1'-yl)-1,4-benzoquinone 2,5-bis-(4'-methoxycarbonyl-1'-methyl-cyclohex-1'-yl)-1,4-benzoquinone 2,5-bis-(4'-n-hexyloxycarbonyl-1'-methyl-cyclohex-1'-yl)-1,4-benzoquinone 2-(5'-methoxycarbonyl-2'-methyl-pent-2'-yl)-1,4-benzoquinone 2-(5'-n-hexyloxycarbonyl-2'-methyl-pent-2'-yl)-1,4-benzoquinone 2-(5'-n-hexyloxycarbonyl-2'-methyl-pent-2'-yl)-5-methyl-1,4-benzoquinone 2-(5'-n-hexyloxycarbonyl-2'-methyl-pent-2'-yl)-6-methyl-1,4-benzoquinone 2-(5'-carboxy-2'-methyl-pent-2'-yl)-5-t-butyl-1,4-benzoquinone 2-(5'-methoxycarbonyl-2'-methyl-pent-2'-yl)-5-t-butyl-1,4-benzoquinone 2-(5'-n-hexyloxycarbonyl-2'-methyl-pent-2'-yl)-5-t-butyl-1,4-benzoquinone 2-(5'-n-dodecyloxycarbonyl-2'-methyl-pent-2'-yl)-5-t-butyl-1,4-benzoquinone 2-(5'-methoxycarbonyl-2'-methyl-pent-2'-yl)-5-(1',1',3',3'-tetramethylbutyl)-1,4-benzoquinone 2,5-bis-(5'-methoxycarbonyl-2'-methyl-pent-2'-yl)-1,4-benzoquinone 2,5-bis-(5'-ethoxycarbonyl-2'-methyl-pent-2'-yl)-1,4-benzoquinone 2,5-bis-(5'-n-propyloxycarbonyl-2'-methyl-pent-2'-yl)-1,4-benzoquinone 2-(5'-n-hexyloxycarbonyl-2'-methyl-pent-2'-yl)-5-(3'-n-hexyloxycarbonyl-2'-methyl-prop-2'-yl)-1,4-benzoquinone 2-(5'-n-hexyloxycarbonyl-2'-methyl-pent-2'-yl)-5-(3'-n-octyloxycarbonyl-2'-methyl-prop-2'-yl)-1,4-benzoquinone 2,5-bis-(5'-iso-propyloxycarbonyl-2'-methyl-pent-2'-yl)-1,4-benzoquinone 2,5-bis-(5'-n-pentyloxycarbonyl-2'-methyl-pent-2'-yl)-1,4-benzoquinone 2,5-bis-(5'-iso-pentyloxycarbonyl-2'-methyl-pent-2'-yl)-1,4-benzoquinone 2,5-bis-(5'-n-hexyloxycarbonyl-2'-methyl-pent-2'-yl)-1,4-benzoquinone 2,5-bis-(5'-n-heptyloxycarbonyl-2'-methyl-pent-2'-yl)-1,4-benzoquinone 2,5-bis-(5'-cyclohexyloxycarbonyl-2'-methyl-pent-2'-yl)-1,4-benzoquinone 2,5-bis-(5'-n-octyloxycarbonyl-2'-methyl-pent-2'-yl)-1,4-benzoquinone 2,5-bis-[5'-(2''-ethylhexyloxycarbonyl)-2'-methyl-pent-2'-yl]-1,4-benzoquinone 2,5-bis-(5'-n-dodecyloxycarbonyl-2'-methyl-pent-2'-yl)-1,4-benzoquinone 2,5-bis-(5'-n-hexadecyloxycarbonyl-2'-methyl-pent-2'-yl)-1,4-benzoquinone 2,5-bis-[5'-(2''-methoxyethoxycarbonyl)-2'-methyl-pent-2'-yl]-1,4-benzoquinone 2,5-bis-[5'-(2''-n-butyloxyethoxycarbonyl)-2'-methyl-pent-2'-yl]-1,4-benzoquinone 2,5-bis-[5'-(2''-cyclohexyloxyethoxycarbonyl)-2'-methyl-pent-2'-yl]-1,4-benzoquinone 2,5-bis-[5'-(2''-allyloxyethoxycarbonyl)-2'-methyl-pent-2'-yl]-1,4-benzoquinone 2,5-bis-[5'-(2''-benzyloxyethoxycarbonyl)-2'-methyl-pent-2'-yl]-1,4-benzoquinone 2,5-bis-[5'-(2''-phenoxyethoxycarbonyl)-2'-methyl-pent-2'-yl]-1,4-benzoquinone 2,5-bis-(5'-phenoxycarbonyl-2'-methyl-pent-2'-yl)-1,4-benzoquinone 2,5-bis-(5'-benzyloxycarbonyl-2'-methyl-pent-2'-yl)-1,4-benzoquinone 2,5-bis-(5'-tetrahydrofurfuryloxycarbonyl-2'-methyl-pent-2'-yl)-1,4-benzoquinone 2,5-bis-(5'-furfuryloxycarbonyl-2'-methyl-pent-2'-yl)-1,4-benzoquinone 2,5-bis-(5'-tetrahydropyran-4''-yloxycarbonyl-2'-methyl-pent-2'-yl)-1,4-benzoquinone 2-(5'-n-hexyloxycarbonyl-2'-methyl-pent-2'-yl)-5-(5'-methoxycarbonyl-2'-methyl-pent-2'-yl)-1,4-benzoquinone 2,5-bis-(5'-carboxy-2'-methyl-pent-2'-yl)-1,4-benzoquinone and its sodium salts 2,5-bis-(5'-carbamoyl-2'-methyl-pent-2'-yl)-1,4-benzoquinone 2,5-bis-(5'-N-n-butylcarbamoyl-2'-methyl-pent-2'-yl)-1,4-benzoquinone 2,5-bis-(5'-N-n-dimethylcarbamoyl-2'-methyl-pent-2'-yl)-1,4-benzoquinone 2,5-bis-(5'-N,N-di-n-butylcarbamoyl-2'-methyl-pent-2'-yl)-1,4-benzoquinone 2,5-bis-(5'-N-eicosylcarbamoyl-2'-methyl-pent-2'-yl)-1,4-benzoquinone 2,5-bis-(5'-N-allylcarbamoyl-2'-methyl-pent-2'-yl)-1,4-benzoquinone 2,5-bis-(5'-N-cyclohexylcarbamoyl-2'-methyl-pent-2'-yl)-1,4-benzoquinone 2,5-bis-(5'-N-benzylcarbamoyl-2'-methyl-pent-2'-yl)-1,4-benzoquinone 2,5-bis-(5'-N-phenylcarbamoyl-2'-methyl-pent-2'-yl)-1,4-benzoquinone 2,5-bis-(5'-morpholinocarbamoyl-2'-methyl-pent-2'-yl)-1,4-benzoquinone 2-(7'-methoxycarbonyl-2',2',4'-trimethyl-hept-4'-yl)-5-t-butyl-1,4-benzoquinone 2-(1',7'-dimethoxycarbonyl-4'-methyl-hept-4'-yl)-1,4-benzoquinone 2,5-bis-(2',6'-dimethyl-8'-hydroxy-oct-2'-yl)-1,4-benzoquinone 2,5-bis-(8'-acetyloxy-2',6'-dimethyl-oct-2'-yl)-1,4-benzoquinone 2,5-bis-(2',6'-dimethyl-8'-propionyloxy-oct-2'-yl)-1,4-benzoquinone 2,5-bis-(8'-butyryloxy-2',6'-dimethyl-oct-2'-yl)-1,4-benzoquinone 2,5-bis-(2',6'-dimethyl-8'-hexanoyloxy-oct-2'-yl)-1,4-benzoquinone 2-(5'-diethylphosphono-5'-ethoxycarbonyl-2'-methyl-pent-2'-yl)-1,4-benzoquinone 2,5-bis-(5',5'-diethoxycarbonyl-2'-methyl-pent-2'-yl)-1,4-benzoquinone 2,5-bis-(2',6'-dimethyl-8'-eicosanoyloxy-oct-2'-yl)-1,4-benzoquinone 2,5-bis-(8'-crotonyloxy-2',6'-dimethyl-oct-2'-yl)-1,4-benzoquinone 2,5-bis-(8'-benzoyloxy-2',6'-dimethyl-oct-2'-yl)-1,4-benzoquinone 2,5-bis-(2',6'-dimethyl-8'-phenacetyloxy-oct-2'-yl)-1,4-benzoquinone 2,5-bis-(8'-cyclohexylcarbonyloxy-2',6'-dimethyl-oct-2'-yl)-1,4-benzoquinone 2,5-bis-(8'-methoxy-2',6'-dimethyl-oct-2'-yl)-1,4-benzoquinone 2,5-bis-(8'-n-butoxy-2',6'-dimethyl-oct-2'-yl)-1,4-benzoquinone 2,5-bis-(6'-amino-2'-methyl-hept-2'-yl)-1,4-benzoquinone and its hydrochloride 2,5-bis-(6'-N-methylamino-2'-methyl-hept-2'-yl)-1,4-benzoquinone 2,5-bis-(6'-N,N-dimethylamino-2'-methyl-hept-2'-yl)-1,4-benzoquinone 2,5-bis-(6'-N-ethylamino-2'-methyl-hept-2'-yl)-1,4-benzoquinone 2,5-bis-(6'-N,N-diethylamino-2'-methyl-hept-2'-yl)-1,4-benzoquinone 2,5-bis-(6'-N-n-butylamino-2'-methyl-hept-2'-yl)-1,4-benzoquinone 2,5-bis-(6'-N,N-di-n-butylamino-2'-methyl-hept-2'-yl)-1,4-benzoquinone 2,5-bis-(2'-methyl-6'-morpholino-hept-2'-yl)-1,4-benzoquinone 2,5-bis-(6'-acetamido-2'-methyl-hept-2'-yl)-1,4-benzoquinone 2,5-bis-(6'-hexanamido-2'-methyl-hept-2'-yl)-1,4-benzoquinone 2,5-bis-(12'-amino-2',12'-dimethyl-tetradec-2'-yl)-1,4-benzoquinone
2,5-bis-(12'-amino-3',13'-dimethyl-tetradec-3'-yl)-1,4-benzoquinone
2,5-bis-(12'-acetamido-2',13'-dimethyl-tetradec-2'-yl)-1,4-benzoquinone
2,5-bis-(12'-acetamido-3',13'-dimethyl-tetradec-3'-yl)-1,4-benzoquinone
2-(2'-methyl-4'-phosphono-but-2'-yl)-1,4-benzoquinone and its sodium salts
2-(2'-methyl-4'-dimethylphosphono-but-2'-yl)-1,4-benzoquinone
2-(4'-diethylphosphono-2'-methyl-but-2'-yl)-1,4-benzoquinone
2-(4'-di-n-butylphosphono-2'-methyl-but-2'-yl)-1,4-benzoquinone
5-t-butyl-2-(2'-methyl-4'-dimethylphosphono-but-2'-yl)-1,4 benzoquinone
5-(1',1',3',3'-tetramethylbutyl)-2-(2'-methyl-4'-dimethylphosphono-but-2'-yl)-1,4-benzoquinone
2,5-bis-(2'-methyl-4'-di-methylphosphono-but-2'-yl)-1,4-benzoquinone
2,5-bis-(2'-methyl-4'-di-ethylphosphono-but-2'-yl)-1,4-benzoquinone
2,5-bis-(2'-methyl-4'-di-n-propylphosphono-but-2'-yl)-1,4-benzoquinone
2-(5'-n-hexyloxycarbonyl-2'-methyl-pent-2'-yl)-5-(2'-methyl-4'-diethylphosphono-but-2'-yl)-1,4-benzoquinone
2,5-bis-(2'-methyl-4'-di-iso-propylphosphono-but-2'-yl)-1,4-benzoquinone
2,5-bis-(2'-methyl-4'-di-n-butyl-phosphono-but-2'-yl)-1,4-benzoquinone
2,5-bis-[2'-methyl-4'-(di-2''-ethylhexyl-phosphono)-but-2'-yl]-1,4-benzoquinone
2,5-bis-(2'-methyl-4'-di-n-dodecylphosphono-but-2'-yl)-1,4-benzoquinone
2,5-bis-[2'-methyl-4'-(2-oxo-1,3,2-dioxaphospholan-2''-yl)-but-2'-yl]-1,4-benzoquinone
2,5-bis-[2'-methyl-4'-methyl-2-oxo-1,3,2-dioxaphospholan-2''-yl)-but-2'-yl]-1,4-benzoquinone
2,5-bis-[4'-(ethyl-ethylphosphino)-2'-methyl-but-2'-yl]-1,4-benzoquinone
2,5-bis-(2'-methyl-3'-sulpho-prop-2'-yl)-1,4-benzoquinone
2-(2'-methyl-3'-sulphonamido-prop-2'-yl)-1,4-benzoquinone
5-t-butyl-2-(2'-methyl-3'-sulphonamido-prop-2'-yl)-1,4-benzoquinone
2-(2'-methyl-3'-N-methylsulphonamido-prop-2'-yl)-1,4-benzoquinone
5-(1',1',3',3'-tetramethylbutyl)-2-(2'-methyl-3'-N-methylsulphonamido-prop-2'-yl)-1,4-benzoquinone
2-(2'-methyl-3'-N,N-di-n-butylsulphonamido-prop-2'-yl)-1,4-benzoquinone
2-(2'-methyl-3'-N-n-octylsulphonamido-prop-2'-yl)-1,4-benzoquinone
5-t-butyl-2-(2'-methyl-3'-N-n-octylsulphonamido-prop-2'-yl)-1,4-benzoquinone
5-t-butyl-2-(2'-methyl-5'-ethyloxycarbonyl-5'-diethylphosphonohex-2'-yl)-1,4-benzoquinone
2,5-bis-(2',6'-dimethyl-7'-carboxy-hept-2'-yl)-1,4-benzoquinone
2,5-bis-(2',6'-dimethyl-7'-methyloxycarbonyl-hept-2'-yl)-1,4-benzoquinone.

The present invention also provides a process for the production of compounds of the formula I comprising oxidising a compound having the formula V:

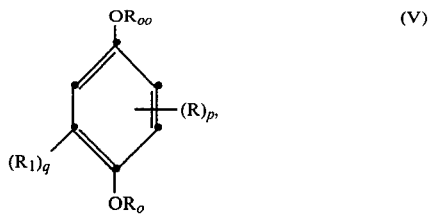

wherein R, $R_1$, p and q are as defined above, and $R_o$ and $R_{oo}$ are, independently, hydrogen or methyl.

Examples of oxidising agents which may be employed are salts of elements capable of abstracting electrons and possessing a suitable redox potential e.g. ferric, cupric, mercuric and ceric salts; silver oxide, silver carbonate, lead tetra acetate, chromic acid and chromates, chromium oxide, e.g. Jones' reagent, manganese dioxide and permanganate salts, hypohalites e.g. sodium hypochlorite; perhalates e.g. sodium perchlorate alone or catalysed with metavanadate salts; nitric acid, nitrates and oxides of nitrogen; oxygen, and air, optionally catalysed by metal salts e.g. copper salts. In addition organic oxidising agents such as chloranil may be used, as well as organometallic or organically-complexed inorganic oxidising agents. Preferred oxidising agents are hypohalite salts, oxygen or air in the presence of copper salts. The reaction is carried out using at least one equivalent of the oxidising agent, and normally an excess of the oxidising agent is used.

The reaction can be carried out in solution or suspension in water or an organic solvent in the temperature range conveniently from 0° to the boiling point of the solvent, preferably 0°–40° C. Optionally the reaction can be carried out in a two phase system in the presence of a phase transfer catalyst as described in British Publication No. 2070003.

Examples of organic solvents which may be used in the process are those stable under the conditions of the reaction and include chloroform, methylene chloride, acetone, benzene, toluene and petroleum ethers.

Any functional derivative of a compound of formula I may be converted to a different functional derivative. For example when Q is the acid group —$CO_2H$ it may be esterified with an alcohol $R_4OH$ to give the corresponding ester —$CO_2R_4$, or when Q is the ester group —$CO_2R_4$ it may be transesterified to give a different $R_4$ group, or alternatively the ester group —$CO_2R_4$ may be converted to an amide —$CON(R_4)(R_5)$ by treatment with $NH(R_4)(R_5)$, wherein $R_4$ and $R_5$ have their previous significance, or where Q is the hydroxyl group OH attached to methylene i.e. —$CH_2OH$, this may be oxidised to a carboxylic acid group with e.g. chromium trioxide.

The starting materials of formula V may be produced by reacting known compounds of formula VI:

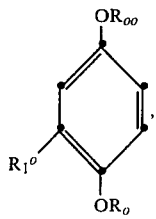 (VI)

wherein $R_1^o$ is hydrogen or $R_1$, and $R_1$, $R_o$ and $R_{oo}$ are as hereinbefore defined with a functional alkylating agent capable of introducing a group of formula II, as hereinbefore defined.

Non-limiting examples of compounds of formula V wherein $R_o$ and $R_{oo}$ are both hydrogen are described in EP patent application no. 69068.

Further examples of compounds of formula V are:
2-(5'-carboxy-2'-methyl-pent-2'-yl)-5-t-butyl-hydroquinone
2,5-bis-(8'-n-butoxy-2',6'-dimethyl-oct-2'-yl)-hydroquinone
5-t-butyl-2-(2'-methyl-5'-ethoxycarbonyl-5'-diethylphosphonohex-2'-yl)-hydroquinone
2-(5'-methoxycarbonyl-2'-methyl-pent-2'-yl)-4-methoxyphenol
3-(5'-methoxycarbonyl-2'-methyl-pent-2'-yl)-4-methoxyphenol
2,5-bis-(5'-methoxycarbonyl-2'-methyl-pent-2'-yl)-4-methoxyphenol
2-(5'-methoxycarbonyl-2'-methyl-pent-2'-yl)-1,4-dimethoxybenzene
2,5-bis-(5'-methoxycarbonyl-2'-methyl-pent-2'-yl)-1,4-dimethoxybenzene.

Functional alkylating agents which are reacted with the hydroquinone VI contain a reactive centre, for example, an olefinic or hydroxy group which is eliminated, transformed or rearranged during the course of the alkylation reaction.

Examples of functional olefins suitable for the functional alkylation of compounds of formula VI are:
5-methylhex-5-enoic acid
methyl 5-methylhex-5-enoate
ethyl 5-methylhex-5-enoate
n-propyl 5-methylhex-5-enoate
iso-propyl 5-methylhex-5-enoate
n-butyl 5-methylhex-5-enoate
iso-butyl 5-methylhex-5-enoate
sec.-butyl 5-methylhex-5-enoate
n-pentyl 5-methylhex-5-enoate
iso-pentyl 5-methylhex-5-enoate
sec.-pentyl 5-methylhex-5-enoate
n-hexyl 5-methylhex-5-enoate
cyclohexyl 5-methylhex-5-enoate
2'-ethylhexyl 5-methylhex-5-enoate
n-octyl 5-methylhex-5-enoate
n-dodecyl 5-methylhex-5-enoate
n-hexadecyl 5-methylhex-5-enoate
methyl 5,7,7-trimethyl-oct-4-enoate
1,7-di-methoxycarbonyl-4-methyl-hept-3-ene
4-carbomethoxy-1-methylcyclohex-1-ene
dimethylprenylphosphonate
diethylprenylphosphonate
dipropylprenylphosphonate
di-isopropylprenylphosphonate
di-n-butylprenylphosphonate
di-n-octylprenylphosphonate
citronellol
citronellyl acetate
citronellyl methyl ether
citronellyl n-butyl ether
2-amino-6-methyl-hept-5-ene
2-amino-6-methyl-hept-6-ene
diethyl 2-ethoxycarbonyl-5-methyl-hex-4-ene-2-phosphonate
ethyl 2-ethoxycarbonyl-5-methyl-hex-4-enoate
2-acetamido-6-methyl-hept-5-ene
2-acetamido-6-methyl-hept-6-ene
2-methyl-2-propene-1-sulphonic acid
2-methyl-2-propene-1-sulphonic acid amide
N-n-butyl-2-propene-1-sulphonic acid amide
N,N-di-n-butyl-2-propene-sulphonic acid amide
N-n-octyl-2-propene-1-sulphonic acid amide Examples of functional hydroxy compounds suitable for the functional alkylation of compounds of formula VI are:
2-amino-6-hydroxy-6-methylheptane
2-acetamido-6-hydroxy-6-methylheptane
11-amino-2,2,12-trimethyl-tridecan-1-ol
as well as members selected from 11-amino-undecanols of the formula:

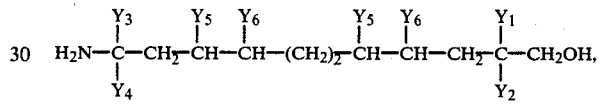

wherein $Y_1$ and $Y_3$, independently, are H or $C_1$–$C_8$ alkyl; $Y_2$ and $Y_4$, independently, are $C_1$–$C_8$ alkyl; and $Y_5$ and $Y_6$, independently, are H or $C_1$–$C_4$ alkyl.

These 11-amino-undecanols are described in more detail, together with their method of manufacture in German Offenlegungschrift No. 2831299.

Alternatively, starting materials of formula V may be produced by reacting compounds of formula VII

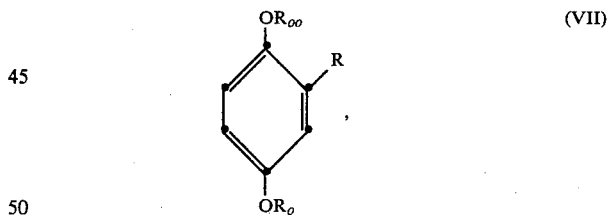 (VII)

wherein R, $R_o$ and $R_{oo}$ have their previous significance, with an alkylating agent capable of introducing a group of formula III as hereinbefore defined.

Examples of olefins suitable for the alkylation of compounds of formula VII are isobutylene and diisobutylene. Examples of alcohols suitable for the alkylation of compounds of formula VII are t-butanol and 1,1,3,3-tetramethylbutan-1-ol.

Any functional derivative of a compound of formula V or VII may be converted to a different functional derivative. For example when Q is the acid group —$CO_2H$ it may be esterified with an alcohol $R_4OH$ to give the corresponding ester —$CO_2R_4$, or when Q is the ester group —$CO_2R_4$ it may be transesterified to give a different $R_4$ group, or alternatively the ester group —$CO_2R_4$ may be converted to an amide —$CON(R_4)(R_5)$ by treatment with $NH(R_4)(R_5)$, wherein $R_4$ and $R_5$ have their previous significance, or where Q is hydroxyl attached to methylene i.e. —CH$_2$OH, it may be oxidised to a carboxylic acid group with e.g. chromium trioxide.

The compounds of formula I provide a valuble means of introducing a wide variety of functional alkyl residues for optimal photographic effect. For example, the polarity of and/or ballast in 1,4-benzoquinones of formula I are able to be regulated, and hence provide an effective control of solubility, compatibility, mobility-/immobility for photographic systems. Such qualities make the 1,4-benzoquinones of formula I valuable intermediates for the preparation of more complex photographically useful compounds, and render them useful as bleaching inhibitors in films of photographic silver dye bleach materials.

The present invention is further illustrated by the following examples in which parts and percentages shown therein are by weight.

EXAMPLE 1

(a) 110 parts of hydroquinone, 284 parts of methyl 5-methyl-hex-5-enoate, and 10 parts of p-toluene sulphonic acid are heated on a steam-bath for 24 hours. The cooled reaction mixture partially solidifies and after trituration with ether, gives after filtration, 2,5-bis-(5'-methoxy-carbonyl-2'-methyl-pent-2'-yl)-hydroquinone, m.p. 150°–153° C. The analytical sample, after crystallisation from methanol water, has m.p. 160°–162° C. with the following percentage composition by weight.

|  | Carbon | Hydrogen |
|---|---|---|
| Found | 67.05 | 8.96 |
| Calculated for $C_{22}H_{34}O_6$ | 66.98 | 8.69 |

(b) 25.0 parts of 2,5-bis-(5'-methoxycarbonyl-2'-methyl-pent-2'-yl)-hydroquinone, 250 parts of glacial acetic acid, and 125 parts of 46% aqueous hydrobromic acid are stored for 15 hours at room-temperature. At the end of this period 2,5-bis-(5'-carboxy-2'-methyl-pent-2'-yl)-hydroquinone containing 0.5 molecule of acetic acid of crystallisation, is filtered off with m.p. 221°–224° C. and with the following percentage composition by weight.

|  | Carbon | Hydrogen |
|---|---|---|
| Found | 63.68 | 8.38 |
| Calculated for $C_{22}H_{30}O_6 \cdot \frac{1}{2}CH_3CO_2H$ | 63.62 | 8.14 |

(c) 44 Parts of 2,5-bis(5'-carboxy-2'-methyl-pent-2'-yl)-hydroquinone are added in portions to 375 parts of 10–14% w/v aqueous sodium hypochlorite solution with vigorous stirring, the temperature being maintained between 25°–30° C. with a cold water bath. The mixture is stirred at room temperature for 1 hour, diluted with 300 parts of water, and acidified with concentrated hydrochloride acid to give, after filtration, 2,5-bis-(5'-carboxy-2'-methyl-pent-2'-yl)-1,4-benzoquinone. After crystallisation from methanol the product has a m.p. of 204°–206° C.

EXAMPLE 2

10.8 Parts of 2,5-bis-(5'-carboxy-2'-methyl-pent-2'-yl)-1,4-benzoquinone, 82 parts of n-hexanol, and 0.5 parts of p-toluene sulphonic acid are heated on a steam bath for 72 hours. The excess n-hexanol is stripped off under reduced pressure, the residue taken up in ether and washed with sodium carbonate solution and then with water. The ethereal solution on evaporation to remove the ether gives a residue which after short path distillation at 0.3 mb gives 2,5-bis-(5'-n-hexyloxycarbonyl-2'-methyl-pent-2'-yl)-1,4-benzoquinone as a yellow solid mp. 45°–47° C. with the following percentage composition by weight.

|  | Carbon | Hydrogen |
|---|---|---|
| Found | 72.15 | 9.86 |
| Calculated for $C_{32}H_{52}O_6$ | 72.14 | 9.84 |

EXAMPLE 3

Similarly to the procedure of Example 2 from methyl alcohol and 2,5-bis-(5'-carboxy-2'-methyl-pent-2'-yl)-1,4-benzoquinone using hydrogen chloride as a catalyst is prepared 2,5-bis-(5'-methoxycarbonyl-2'-methyl-pent-2'-yl-1,4-benzoquinone as a bright yellow crystalline solid m.p. 85°–87° C. with the following percentage composition by weight.

|  | Carbon | Hydrogen |
|---|---|---|
| Found | 67.56 | 8.20 |
| Calculated for $C_{22}H_{32}O_6$ | 67.32 | 8.22 |

EXAMPLE 4

0.9 Parts of 2,5-bis-(5'-methoxycrbonyl-2'-methyl-pent-2'-yl)-1,4-benzoquinone, 16.4 parts of n-hexanol, and 0.1 parts of p-toluene sulphonic acid are heated on a steam bath for 6 hours. The reaction mixture is diluted with ether, washed firstly with a dilute solution of sodium hydroxide, then with water and evaporated to leave a residue. The excess n-hexanol is stripped off under reduced pressure (15,6 mb) and the residual quinone distilled by short-path distillation at 0,2 mb to give 2,5-bis-(5'-n-hexyloxycarbonyl-2'-methyl-pent-2'-yl)-1,4-benzoquinone as a yellow solid identical with the product of Example 1 and with the following percentage composition by weight.

|  | Carbon | Hydrogen |
|---|---|---|
| Found | 72.29 | 9.73 |
| Calculated for $C_{32}H_{52}O_6$ | 72.14 | 9.84 |

EXAMPLE 5

10 Parts of 2,5-bis-(5'-methoxycarbonyl-2'-methyl-pent-2'-yl)-hydroquinone, is dissolved in 174 parts of chloroform and to this solution is added 1 part of tetrabutylammonium hydrogen sulphate in 125 parts of 10–14% aqueous sodium hypochlorite. The resulting two phase system is stirred vigorously for 30 minutes at 25° C. The reaction mixture is then extracted with ether and the ether extract washed with water. The ether solution is then stripped down under reduced pressure to give a residual yellow oil. This oil is taken up in methanol, filtered and the filtrate allowed to stand at 25° C. The product, 2,5-bis-(5'-methoxycarbonyl-2'-methyl-pent-2'-yl)-1,4-benzoquinone, crystallises as yellow prisms from this methanolic solution, and is identical to the product of Example 3.

EXAMPLE 6

(a) 12.4 Parts of 2-methylhydroquinone, 14.2 parts of methyl 5-methylhex-5-enoate, and 0.5 parts of p-toluene sulphonic acid are heated on a steam bath for 24 hours. The cooled reaction mixture is treated with ether, washed firstly with a 10% aqueous solution of sodium hydroxide, and then with water until the aqueous phase is neutral. The ethereal layer is separated and evaporated to give a viscous oil which after short-path distillion at 0.13 mb gives methyl 5-(2',5'-dihydroxy-4'-methyl-phenyl)-5-methyl-hexenoate with the following percentage composition by weight.

|  | Carbon | Hydrogen |
| --- | --- | --- |
| Found | 67.37 | 8.27 |
| Calculated for $C_{15}H_{22}O_4$ | 67.64 | 8.32 |

(b) Similarly to the procedure of Example 5 using methyl 5-(2',5'-dihydroxy-4'-methyl-phenyl)-5-methyl-hexanoate is prepared 2-(5'-n-hexyloxycarbonyl-2'-methyl-pent-2'-yl)-5-methyl-1,4-benzoquinone as an oil with a percentage composition by weight which agrees with that calculated for $C_{20}H_{30}O_4$.

EXAMPLE 7

Similarly to the procedure of Example 5 using 5-(4'-t-butyl-2',5'-dihydroxyphenyl)-5-methyl-hexanoic acid is prepared 2-t-butyl-5-(5'-carboxy-2'-methyl-pent-2'-yl)-1,4-benzoquinone as yellow prisms m.p. 143°–146° C.

EXAMPLE 8

5.5 Parts of hydroquinone, 21.2 parts of n-hexyl 5-methyl-hex-5-enoate, and 1.0 parts of p-toluene sulphonic acid are heated on a steam bath for 4 days. The cooled reaction mixture is taken up in ether, washed with 10% sodium hydroxide solution and then with water, until neutral. After stripping, the residual oil which partially solidified, is triturated with 40°–60° petroleum ether and gives 2,5-bis-(5'-n-hexyloxycarbonyl-2'-methyl-pent-2'-yl)-hydroquinone m.p. 77°–78°. A further crystallisation from 60°–80° petroleum ether gives material m.p. 83°–86° C.

Similarly to the procedure of Example 5 using 2,5-bis-(5'-n-hexyloxycarbonyl-2'-methyl-pent-2'-yl)-hydroquinone is prepared 2,5-bis-(5'-n-hexyloxycarbonyl-2'-methyl-pent-2'-yl)-1,4-benzoquinone identical with the product from Example 2.

EXAMPLE 9

2.0 Parts of 2,5-bis-(5'-n-heptyloxycarbonyl-2'-methyl-pent-2'-yl)-hydroquinone in 25 parts of acetone is triturated with Jones reagent (for preparation see Bowers, Halsall, Jones and Lemin, J.Chem. Soc., 2555, 1953) until a permanent brown colour indicates that oxidation is complete. The reaction mixture is, after dilution with water, extracted with ether, and the ether extract washed with water and evaporated. Short path distillation of the residue at 0.6 mb gives 2,5-bis-(5'-n-heptyloxycarbonyl-2'-methyl-pent-2'-yl)-1,4-benzoquinone as a yellow oil.

Examples 10 to 17 in the following table further exemplify benzoquinones prepared from the corresponding hydroquinone according to the procedure described in Example 9.

| Example | 2,5-Substituents on -1,4-benzoquinone | b.p./mb or m.p. (°C.) |
| --- | --- | --- |
| 10 | bis-5-('-ethylhexyloxy-carbonyl)-2-methyl-pent-2-yl | 250/0.6 |
| 11 | bis-(5-cyclohexyloxycarbonyl-2-methyl-pent-2-yl) | 136–138 |
| 12 | cis/trans-bis-(4-methoxycarbonyl-1-methyl-cyclohex-1-yl) | 160–170 |
| 13 | bis-(8-acetyloxy-2,6-dimethyl-oct-2-yl) | 250/1 |
| 14 | bis-(8-n-butoxy-2,6-dimethyl-oct-2-yl) | 250/0.6 |
| 15 | 2-t-butyl-dimethyl 5-(2-methyl-but-2-yl-4-phosphonate) | 105–7 |
| 16 | 2-t-butyl-diethyl 5-(5'-ethoxycarbonyl-2'-methyl-hex-2'-yl-5-phosphonate) | 69–71 |
| 17 | bis-(5-isopropyloxycarbonyl-2-methyl-pent-2-yl) | oil |

EXAMPLE 18

2.0 Parts of 2,5-bis-(2',6'-dimethyl-8'-hydroxy-oct-2'-yl)-hydroquinone in 20 parts of acetone is oxidised with Jones reagent and worked up by the procedure of Example 9 to give 2,5-bis-(2',6'-dimethyl-7'-carboxy-hept-2'-yl)-1,4-benzoquinone. This acid after esterification with methanol gives the corresponding dimethyl ester after a short-path distillation at 0.7 mb.

EXAMPLE 19

(a) 100 Parts of 98% sulphuric acid are added to 32 parts of methanol keeping the temperature below 10°. To this solution is then added 35.5 parts of methyl 5-methyl-hex-5-enoate followed by 12.4 parts of hydroquinone monomethyl ether. After stirring for 24 hours at room temperature the reaction mixture is poured into water, and the oil which separated extracted with ether. The ether extract after washing with 2N sodium hydroxide solution and then water is evaporated. Dilution of this oil with 40°–60° petroleum ether containing a little ether gives 2,5-bis-(5'-methoxy-carbonyl-2'-methyl-pent-2'-yl)-4-methoxyphenol m.p. 82°–84° C. with the following percentage composition by weight.

|  | Carbon | Hydrogen |
| --- | --- | --- |
| Found | 67.99 | 9.16 |
| Calculated for $C_{23}H_{36}O_6$ | 67.62 | 8.88 |

(b) 4.1 Parts of 2,5-bis-(5'-methoxycarbonyl-2'-methyl-pent-2'-yl)-4-methoxyphenol in 30 parts of acetone is oxidised with Jones reagent and worked up according to the procedure of Example 9. Crystallisation of the reaction product from methanol and water gives 2,5-bis-(5'-methoxycarbonyl-2'-methyl-pent-2'-yl)-1,4-benzoquinone m.p. 84°–86° C. which is indentical with that obtained in Example 3.

EXAMPLE 20

(a) To 13.6 parts of aluminium chloride in 25 parts of nitro-methane is added 13.8 parts of hydroquinone dimethyl ether and 14.2 parts of methyl 5-methyl-hex-5-enoate dissolved in 25 parts of nitro-methane dropwise at room temperature. The reaction mixture is stored at room temperature for 2 days before being poured into water. The organic phase is ether extracted, and the ether extract is washed in turn with water, 2N sodium hydroxide solution, water, and then evaporated and gives bis-2,5-(5'-methoxycarbonyl-2'-methyl-pent-2'- yl)-1,4-dimethoxybenzene mb$_{0.4}$ 220° C. and m.p. 81°–83° C. after a crystallisation from 40°–60° petroleumether.

$$CH_3CO-(CH_2)_2-\underset{\underset{CH_3}{|}}{CH}-(CH_2)_3-C(CH_3)_2$$

|  | Carbon | Hydrogen |
|---|---|---|
| Found | 68.48 | 9.12 |
| Calculated for C$_{24}$H$_{38}$O$_6$ | 68.22 | 9.06 |

(b) 2,5-Bis-(5'-methoxycarbonyl-2'-methyl-pent-2'-yl)-1,4-dimethoxybenzene by the same oxidation procedure as Example 9 gives 2,5-bis-(5'-methoxycarbonyl-2'-methyl-pent-2'-yl)-1,4-benzoquinone identical with that obtained in Example 3.

EXAMPLE 21

(a) 62.0 Parts of hydroquinone monoethyl ether, 28,4 parts of methyl 5-methyl-hex-5-enoate, and 2.0 parts of p-toluene sulphonic acid are heated on a steam-bath for 5 days. The reaction mixture is then diluted with ether and washed first with 2N sodium hydroxide solution and then water. After evaporation of the ether, the residue is distilled to give 2-(5'-methoxycarbonyl-2'-methyl-pent-2'-yl)-4-methoxy-phenol with mb$_{0.1}$ 154° C. and the following percentage by weight.

|  | Carbon | Hydrogen |
|---|---|---|
| Found | 67.92 | 8.56 |
| Calculated for C$_{15}$H$_{22}$O$_4$ | 67.65 | 8.33 |

(b) 9.0 Parts of 2-(5'-methoxycarbonyl-2'-methyl-pent-2'-yl)-4-methoxyphenol in 50 parts acetone after oxidation with Jones reagent yields 2-(5'-methoxycarbonyl-2'-methyl-pent-2'-yl)-1,4-benzoquinone mb$_{0.9}$ 140°–144° C. with the following percentage by weight.

|  | Carbon | Hydrogen |
|---|---|---|
| Found | 67.10 | 7.30 |
| Calculated for C$_{14}$H$_{18}$O$_4$ | 67.18 | 7.25 |

EXAMPLE 22

The following layer is coated on a transparent cellulose acetate support. This layer contains per m$^2$:
12 g of gelatin,
0.26 g of the dye of the formula 0.59 g of silver (in the form of a silver bromide emulsion),
0.80 g of 1,3-dichloro-triazine-5-aminobenzene-4'-sulphonic acid as hardener for the gelatin and
0.17 g of a finely dispersed compound of the formula (100)

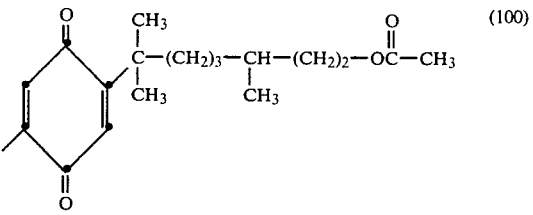

as bleaching inhibitor.

The same photographic element is prepared, but without bleaching inhibitor.

Two strips of each of these elements are exposed with light (500 Lux) through a step wedge for 1 second. One strip of each of these elements is then treated at 24° C. as follows:

| (A) |  |  |  |
|---|---|---|---|
|  | 1. Developing | 8 minutes | bath 1 |
|  | 2. Bleaching | 4 minutes | bath 2 |
|  | 3. Fixing | 3 minutes | bath 3 |
|  | 4. Washing | 3 minutes |  |

The second strip of each of these elements is treated as follows:

| (B) |  |  |  |
|---|---|---|---|
|  | 1. Developing | 8 minutes | bath 1 |
|  | 2. Fixing | 3 minutes | bath 3 |
|  | 3. Washing | 3 minutes |  |

The baths have the following composition

| Bath 1: Developing |  |  |
|---|---|---|
| ethylenediamine tetraacetic acid tetrasodium salt | 2 | g |
| potassium hydroxyde 85% | 22 | g |
| potassium metabisulfite | 15 | g |
| boric acid | 13.35 | g |
| potassium bromide | 1.65 | g |
| benztriazol | 0.25 | g |
| phenidone | 2.5 | g |
| hydroquinone | 8.35 | g |
| ascorbic acid | 8.35 | g |
| water to make up | 1000 | ml |
| Bath 2: Bleaching |  |  |
| m-nitrobenzenesulfonic acid | 12 | g |
| sulfaminic acid | 280 | g |
| ethylcellosolve | 120 | ml |
| 2,3-dimethylquinoxaline | 4 | g |
| potassium iodide | 12 | g |
| water to make up | 1000 | ml |
| Bath 3: Fixing |  |  |
| ethylenediamine tetracetic acid, | 3 | g |
| ammonium thiosulfate 60% | 333 | g |

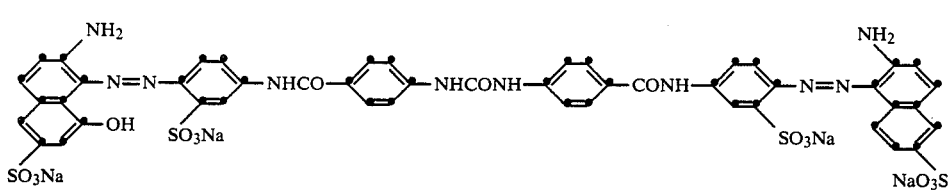

| -continued | |
|---|---|
| ammonium bisulfite 60% | 75 g |
| ammonia | 21 ml |
| water up to | 1000 ml |

According to (A) a clear, sharp magenta wedge is obtained for both elements and according to (B) a silver wedge is obtained, which is overlayed by the dye. The silver density of the wedge obtained according to (A) is measured with a remission sensitometer in the green spectrum range. The maximum silver density is 1.80.

The silver density is measured with the same sensitometer in the red spectrum range.

The free element containing no bleaching inhibitor has a silver amount with a density of 0.5 and is able to bleach the magenta dye up to a density of 0.5. On the other hand the element containing a bleaching inhibitor is able to bleach, with an equal amount of silver, the magenta dye only up to a density of 1.25. [This dyestuff bleaching is inhibited by the compound of the formula 100].

By using in place of the compound of formula (100) a equal amount of another bleaching inhibitor of formulae

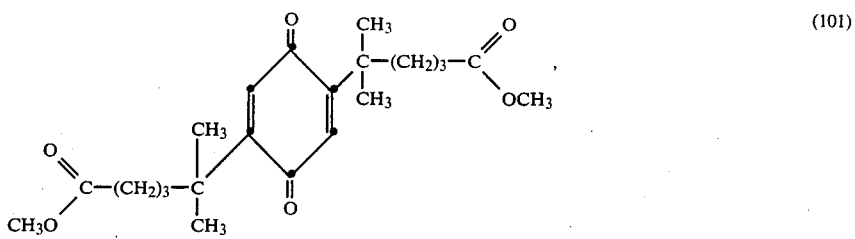
(101)

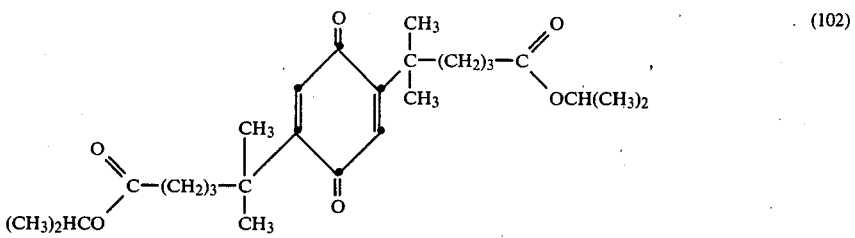
(102)

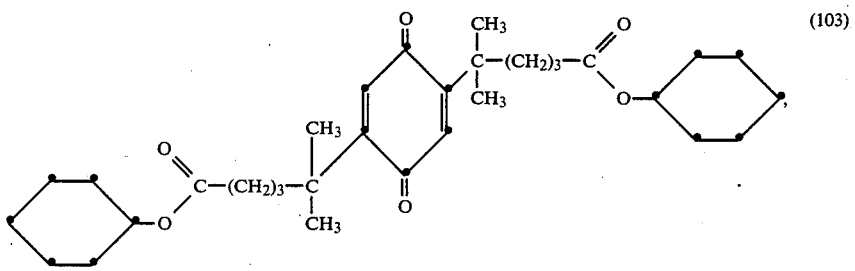
(103)

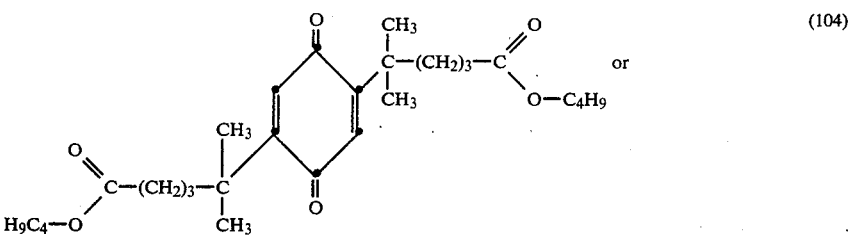
(104)

or

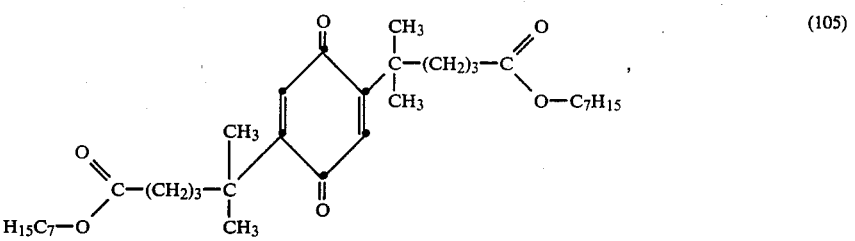
(105)

the following magenta density values are obtained after exposure and working up:
compound (101): 1.20
compound (102): 1.05
compound (103): 1.30
compound (104): 1.00
compound (105): 0.90

EXAMPLE 23

4 photographic elements are processed to form a negative cyan-image according to the silver dye bleaching process:

Element A: the following layers are coated on a transparent polyester support:

a dyestuff layer containing per m² 1.6 g of gelatin, 0.135 g of the bluish grenn dye of the formula

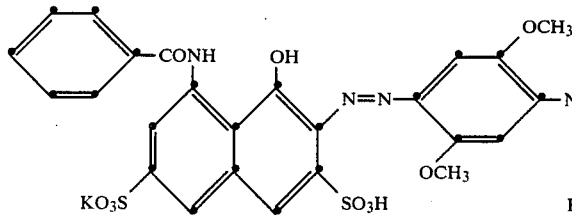 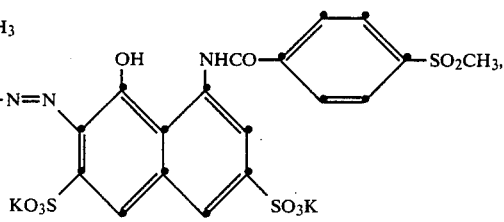

0.05 mg of red, colloidal gold as developing wedge and 40 mg of 1-amino-3-hydroxy-5-methylmorpholinium-triazine-tetrafluoroborate as hardener;

a layer containing per m² 1 g of gelatin, 0.5 g of a compound of formula (100) and 20 mg of said hardener and a layer containing per m² 1.8 g of gelatin, 0.4 g of silver as red sensitive silver chlorobromide emulsion with 25 mol.% silver chloride and a middle particle size of 0.3 μm, and 40 mg of said hardener.

Element B: is prepared like element A, but without bleaching inhibitor in the second layer.

Element D: is prepared like element C, but with 1 g/m² of the compound of formula (100) in the third layer.

Test samples of the elements A to D are exposed in a sensitometer with red light and then processed as follows:

1. Silver developing for 3 minutes at 30° C. in a bath of the following composition:

| ethylenediamine tetraacetic acid, tetrasodium salt | 4 g |
|---|---|
| potassium sulfite | 19.9 g |
| sodium sulfite, anhydrous | 38.0 g |
| hydroquinone | 8.0 g |
| 1-phenyl-4-methylpyrazolidon | 0.5 g |
| potassium carbonate, anhydrous | 19.5 g |
| potassium bicarbonate | 13.3 g |
| potassium bromide | 3.5 g |
| benztriazol | 1.0 g |
| ethylcellosolve | 57.4 g |
| sodium thiosulfate, anhydrous | 0.9 g |
| water to make up | 1000 ml |

A negative silver-image is formed in the third layer and a positive silver image in the first layer by silver complex diffusion and silver deposit at the developing nuclei.

2. Washing for 1 minute.
3. Simultaneous dye and silver bleaching during 3 minutes at 30° C. in a bleaching bath of the following composition:

| sulfuric acid | 41.8 g |
|---|---|
| sodium m-nitrobenzenesulfonate | 7.5 g |
| ethylcellosolve | 57.4 g |
| 2,3,6-trimethylquinoxaline | 1.1 g |
| potassium iodide | 9.0 g |
| sodium bis-(β-cyanoethyl)-sulfoethyl- | 2.9 g |
| phosphine | |
| water to make up | 1000 ml |

4. Washing for 1 minute
5. Fixing for 3 minutes at 30° C. in a fixing bath of composition according to example 1.
6. Washing for 4 minutes and drying of the elements.

The dyestuff image (of all the 4 elements) obtained is a counter-image of the exposure wedge. The maximum dyestuff density therein has the following values:

| Element | A | B | C | D |
|---|---|---|---|---|
| maximum density | 1.0 | 0.58 | 0.35 | 0.80 |

On comparing the maximum density of the 4 elements with the maximum density of the corresponding test samples, which are fixed directly after the developing (100%), the following dyestuff loss results for A to B are obtained:

| Element | A | B | C | D |
|---|---|---|---|---|
| dyestuff loss | 0% | 42% | 45% | 20% |

What we claim is:
1. A benzo-1,4-quinone compound of the formula I

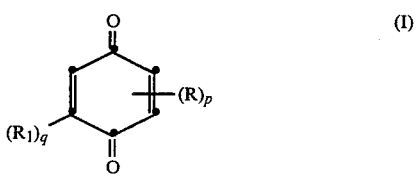

wherein
p is 1 or 2 and q is 0 or 1, provided that p+q is 1 or 2 and the R and $R_1$ substituents present are present in the 2- or 2- and 5-positions of the ring;
R is a radical of formula II

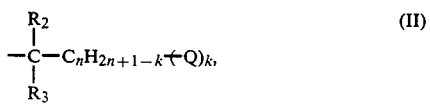

and
Q is a member selected from the group consisting of $-CO_2R_4$, $-CON(R_4)(R_5)$, $-OR_5$, $-OCOR_7$, $-N(R_8)(R_9)$, $-SO_2R_{12}$, $-CN$, Halogen, $-NO_2$ or $-COR_{13}$,
n is an integer from 1 to 20, and k is 1 or 2, $R_1$ is $C_1$–$C_8$ straight or branched chain alkyl, or a radical of formula II as hereinbefore defined, and when $R_1$ is a radical of formula II, then $R_1$ and R may be the same or different;

$R_2$ and $R_3$ are the same or different and each is straight or branched chain alkyl having from 1 to 5 carbon atoms and, when Q is —$CO_2R_4$, either $R_2$ or $R_3$ is unsubstituted or is substituted by —$CO_2R_4$, the $R_4$ groups being independent, or $R_2$ or $R_3$ may be so linked to the radical $C_nH_{2n+1-k}$ that there is formed a $C_5$–$C_{12}$ cycloalkylene radical substituted by the group —$(CO_2R_4)_k$, the $R_4$ groups being independent, and $R_4$ independently is H, a straight or branched chain alkyl having from 1 to 20 carbon atoms or such alkyl interrupted by 1 to 5 oxygen atoms, such groups being unsubstituted or substituted by a group —$OR_6$ wherein $R_6$ is $C_3$–$C_{12}$ cycloalkyl, straight or branched $C_3$–$C_{20}$ alkenyl, $C_6$–$C_{10}$ aryl which is substituted or unsubstituted by 1 or 2 $C_1$–$C_4$-alkyl groups, or $C_7$–$C_{13}$ aralkyl; or $R_4$ is a divalent straight- or branched alkylene group having 2 to 20 carbon atoms, a straight or branched chain alkenyl group having from 3 to 20 carbon atoms, a cycloalkyl group having from 3 to 12 carbon atoms, an aryl group having from 6 to 10 carbon atoms which is unsubstituted or substituted by a $C_1$–$C_4$ alkyl group; or an aralkyl group having from 7 to 13 carbon atoms, a 5- or 6-membered heterocyclic containing an oxygen atom selected from tetrahydrofuranyl and tetrahydropyranyl and which groups are unsubstituted or substituted by one or two $C_1$–$C_4$ straight or banched chain alkyl groups; or methyl substituted by a 5- or 6-membered heterocyclic containing an oxygen atom selected from furfuryl, tetrahydrofurfuryl or tetrahydropyran-2-yl-methyl and which groups are unsubstituted or substituted by one or two $C_1$–$C_4$ straight- or branched chain alkyl groups;

$R_5$ is hydrogen or a straight or branched chain alkyl group having from 1 to 20 carbon atoms, or $R_4$ and $R_5$ together with the nitrogen atom to which they are each bonded may form a saturated 5- or 6-membered heterocyclic ring selected from pyrrolidino, piperidino and morpholino, which groups are unsubstituted or substituted by one or two $C_1$–$C_4$ alkyl groups, $R_7$ is H or a straight or branched chain alkyl group having from 1 to 20 carbon atoms, a straight or branched chain alkenyl having from 3 to 20 carbon atoms, a $C_3$–$C_{12}$ cycloalkyl group, a $C_7$–$C_{13}$ aralkyl group, or a $C_6$–$C_{10}$ aryl group which is unsubstituted or substituted by 1 or 2 $C_{1-4}$-alkyl groups, $R_8$ is H or a straight or branched chain alkyl group having from 1 to 4 carbon atoms, and $R_9$ is H, a straight or branched chain alkyl group having 1 to 4 carbon atoms, or an acyl group of the formula —$COR_7$ wherein $R_7$ is as previously defined, or $R_8$ and $R_9$, together with the nitrogen atom to which they are each bonded, form a saturated 5- or 6-membered ring selected from pyrrolidino, piperidino and morpholino, which groups are unsubstituted or substituted by one or two $C_1$–$C_4$ alkyl groups, and when x is 1, and $R_{12}$ is —OH, —Cl or —$N(R_5)(R_7)$ wherein $R_5$ and $R_7$ are as previously defined, $R_{13}$ is —H, a straight- or branched chain alkyl group having 1 to 20 carbon atoms or halogen, provided that, when $R_{12}$ is —OH, then $R_1$ is a radical of formula II, or a salt thereof with an organic or inorganic acid or base.

2. A compound according to claim 1 wherein the groups R and $R_1$ are present and are bonded in the 2- and 5-positions, respectively, in the benzo-1,4-quinone ring.

3. A compound according to claim 1, wherein $R_1$ is a group of formula III

wherein A is an alkyl group having from 1 to 5 carbon atoms.

4. A compound according to claim 1, wherein R is a group of formula II, wherein Q is —$CO_2R_4$, —$OCOR_7$ or —CN.

5. A compound according to claim 4, wherein R and $R_1$ each represent a group of formula II, wherein Q is —$CO_2R_4$ and $R_4$ is an alkyl group having from 1 to 12 carbon atoms which is unsubstituted or substituted by cycloalkyloxy having from 3 to 12 carbon atoms or by aryloxy having from 6 to 10 carbon atoms, or $R_4$ is a cycloalkyl having from 3 to 12 carbon atoms, aryl having from 6 to 10 carbon atoms, $C_7$–$C_{13}$ aralkyl or methyl substituted by a 5- or 6-membered heterocyclic ring containing an oxygen atom selected from furfuryl, tetrahydrofurfuryl or tetrahydropyran-2-yl-methyl, or Q is —$OCOR_7$, wherein $R_7$ is H, $C_1$–$C_{20}$ alkyl, $C_3$–$C_{12}$ cycloalkyl, $C_7$–$C_{13}$ aralkyl or unsubstituted $C_6$–$C_{10}$ aryl, $R_2$ and $R_3$, independently, are —H or $C_1$–$C_5$ alkyl, p and q are 1 and k and n are as defined in claim 4.

6. A compound according to claim 5 of formula IV

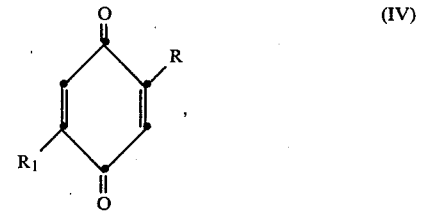

wherein R and $R_1$ each is a group of formula II, wherein Q is —$CO_2R_4$ and $R_4$ is $C_1$–$C_8$ alkyl or $C_5$–$C_8$ cycloalkyl, or Q is —$OCOR_7$, wherein $R_7$ is —H or $C_1$–$C_4$ alkyl, $R_2$ and $R_3$ are each methyl, k is 1 and n is an integer from 1 to 10.

7. A compound according to claim 6, wherein Q is —$CO_2R_4$, $R_2$ and $R_3$ each are methyl, $R_4$ is $C_1$–$C_8$ alkyl, k is 1 and n is 3.

8. A compound according to claim 5, wherein Q is a member selected from —$CO_2R_4$, —$CON(R_4)(R_5)$, —$OR_5$, —$OCOR_7$, —$N(R_8)(R_9)$, —$SO_2R_{12}$ and —CN, k, p, q, n, R, $R_1$ to $R_3$, $R_5$ to $R_9$ and $R_{12}$ are as defined in claim 1 and $R_4$ independently is H, a straight or branched chain alkyl having from 1 to 20 carbon atoms, or such alkyl interrupted by 1 to 5 oxygen atoms, such groups being unsubstituted or substituted by —$OR_6$ wherein $R_6$ is as defined in claim 1 or $R_4$ is a straight or branched chain alkenyl having from 3 to 20 carbon atoms, cycloalkyl having from 3 to 12 carbon atoms, aryl having from 6 to 10 carbon atoms which is unsubstituted or substituted by a $C_1$–$C_4$ alkyl group; or aralkyl having from 7 to 13 carbon atoms, a 5- or 6-membered heterocyclic containing an oxygen atom selected from tetrahydrofuranyl and tetrahydropyranyl which groups are unsubstituted or substituted by one or two $C_1$-$C_4$ straight- or branched chain alkyl groups; or methyl substituted by a 5- or 6-membered heterocyclic containing an oxygen atom selected from furfuryl, tetrahydrofurfuryl or tetrahydropyran-2-yl-methyl which groups are unsubstituted or substituted by one or two $C_1$-$C_4$ straight- or branched chain alkyl groups.

* * * * *